United States Patent [19]

Lasner et al.

[11] Patent Number: 4,962,758

[45] Date of Patent: Oct. 16, 1990

[54] VIBRATORY DEVICE FOR RELEASING AIR BUBBLES TRAPPED IN THE HEART MUSCLE

[76] Inventors: Jeffrey Lasner; Michael Lasner, both of 4 Baltusrol Dr., Purchase, N.Y. 10577

[21] Appl. No.: 364,520

[22] Filed: Jun. 9, 1989

Related U.S. Application Data

[63] Continuation-in-part of Ser. No. 275,679, Nov. 23, 1988, abandoned, which is a continuation-in-part of Ser. No. 126,031, Nov. 27, 1987, abandoned.

[51] Int. Cl.$^5$ .......................... A61H 1/00; A61H 7/00
[52] U.S. Cl. ......................................... 128/41; 128/64
[58] Field of Search ....................... 128/41, 44, 49, 64

[56] References Cited

U.S. PATENT DOCUMENTS

| | | | |
|---|---|---|---|
| 2,826,193 | 3/1958 | Vineberg | 128/64 |
| 2,912,976 | 11/1959 | Grund | 128/49 UX |
| 3,371,662 | 3/1968 | Heid et al. | 128/64 X |
| 3,747,594 | 7/1973 | Bishop | 128/49 |
| 4,048,990 | 9/1977 | Goetz | 128/64 |

Primary Examiner—Edgar S. Burr
Assistant Examiner—Moshe I. Cohen
Attorney, Agent, or Firm—Alfred E. Miller

[57] ABSTRACT

A hand-held vibratory device for releasing bubbles of air which remain in the heart muscles after open heart surgery and which are normally difficult to release due to surface tension. The vibratory device includes a power source and a replaceable heart cradle support member having a soft and pliable heart engaging element.

9 Claims, 6 Drawing Sheets

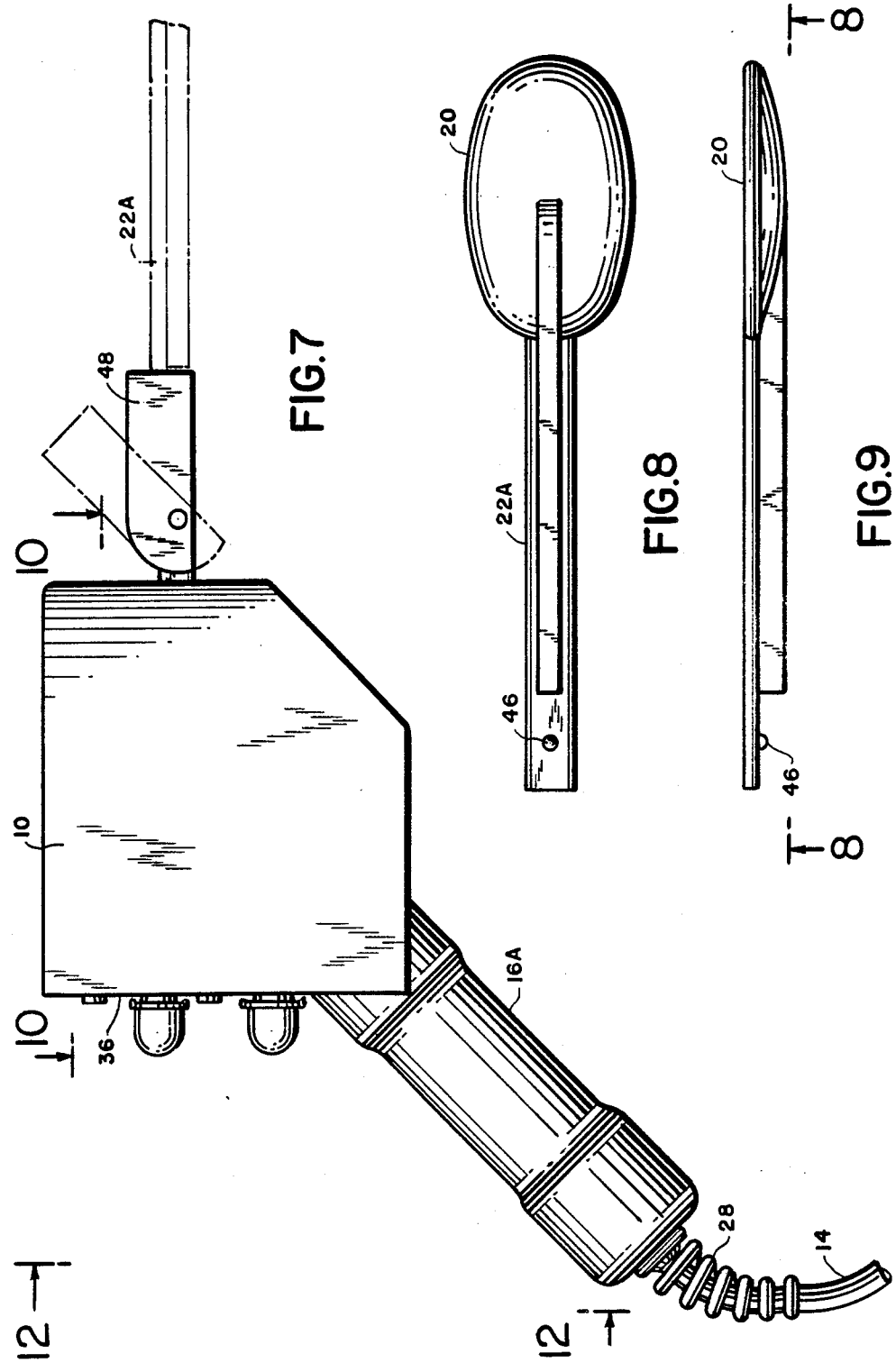

FIG.12
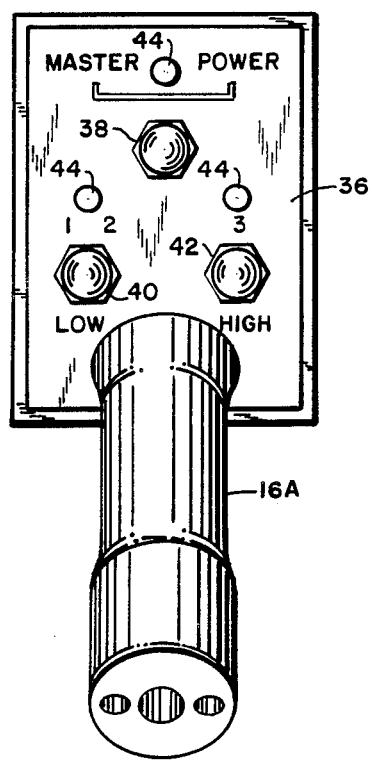
FIG.13
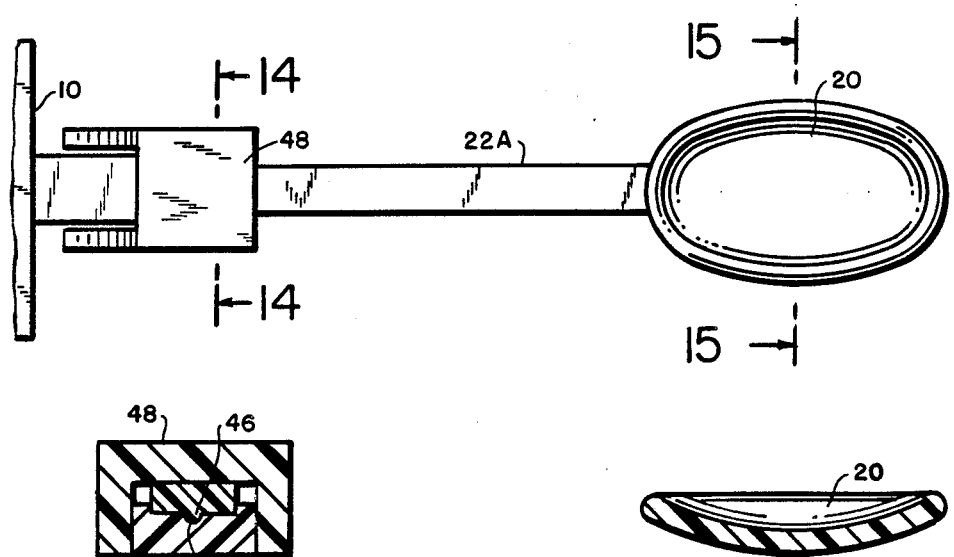
FIG.14
FIG.15

VIBRATORY DEVICE FOR RELEASING AIR BUBBLES TRAPPED IN THE HEART MUSCLE

This application is a continuation-in-part of application Ser. No. 275,679, filed 11/23/88, now abandoned, which is a continuation-in-part of Ser. No. 126,031, abandoned, filed 11/27/87.

The present invention relates to a hand-held device for releasing entrapped air bubbles in the muscles of the heart.

It is known that air bubbles in the circulatory system of a human can be potentially dangerous since they can move in the blood stream through the system to a location in the anatomy with serious or fatal consequences.

In open-heart surgery, the surgeon is often faced with the problem of eliminating air bubbles that are trapped in the papillary muscles of the heart. Prior to the present invention, a usual procedure of the surgeon was to gently massage the heart, with suction catheters in place, prior to suturing the chest, for removing the air bubbles that were introduced during surgery. However, the surgeon often could not be assured that all the air bubbles had been released from their entrapment and thereby avoid potentially serious after-consequences. As is known, it is often difficult to free up the air bubbles because of surface tension. Consequently, there is a need for a device that engages the heart and which operates to liberate the air bubbles from entrapment in the heart muscle.

It is an object of the present invention to provide a vibratory device which engages and cradles the heart for massaging the same whereby the entrapped air bubbles in the heart muscle are released to the atmosphere, or to a common high point to facilitate the gathering and removal of air through a secondary device, such as a suction catheter or a needle attached to a syringe, for the suction of said air.

It is a further object of the present invention to provide a heart vibrator that has a heart contacting surface that is soft and pliable.

It is another object of the present invention to provide a heart cradling member which is removably attached to a vibratory device, and which is designed to be disposable.

It is still another object of the present invention to provide a vibratory device in which the heart-engaging surfaces are either stiff or moldable to the heart configuration.

It is another object of the present invention to have a multiplicity of disposable soft heart-cradling members of graduated sizes for selection depending upon the heart size.

In order that the present invention will be more clearly understood, it will now be disclosed in greater detail with reference to the accompanying drawings in which:

FIG. 7 is a side elevational view of an alternate embodiment of the present invention.

FIG. 8 is a top plan view of the heart cradle device shown detached from the vibratory device.

FIG. 9 is a view of the cradle device taken along the lines 8—8.

FIG. 12 is a view of the vibratory device controls taken along the lines 12—12 of FIG. 7.

FIG. 13 is a top plan view of the cradle device connected to a part of the vibratory device.

FIG. 14 is a view taken along the lines 14—14 of FIG. 13 and

FIG. 15 is a view taken along the lines 15—15 of FIG. 13

Figure 1:
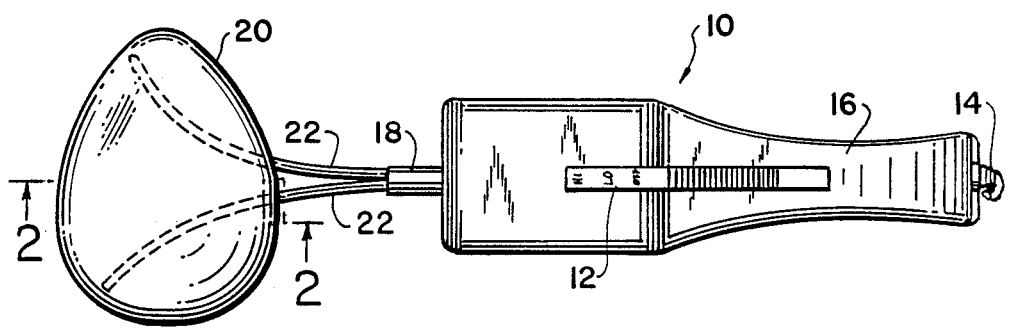
FIG. 1 is a top plan view of the vibrator device for releasing entrapped air bubbles in the muscles of the heart in accordance with the teachings of my present invention.
Figure 2:
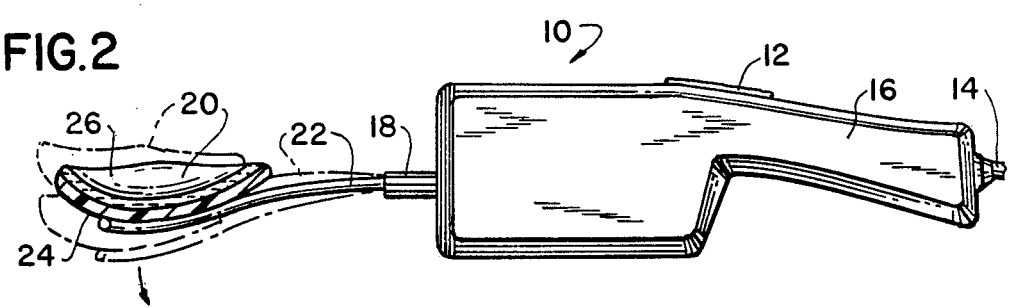
FIG. 2 is a side elevation view of FIG. 1 showing the device in a vibratory mode in dashed lines.

Referring to the drawings, a vibrator is referred to generally by the reference numberal 10 and constitutes a known electro-mechanical device employing an armature which is free to oscillate in a magnetic field that can be used for massage purposes on the human body. Consequently, the vibrator device 10 generates a rapidly acting oscillating motion which is utilized in the present invention. As seen in FIGS. 1 and 2 the massage device 10 is provided with an on-off, low-high switch 12 for operating the device which is connected to a line cord 14 that derives power from an A/C outlet (not shown). In the alternative, it is possible to provide a vibrator device for the present invention which is battery operated, and is preferable rechargeable. The vibrating device is also provided with a handle 16 for grasping by the user. A pair of sleeves 18 is shown projecting from the vibrator 10, and through which oscillations are transmitted to a heart support and cradle device 20. This heart support device is attached to rods 22 which are removably mounted within bores 19 in the sleeves 18.

Figure 3:
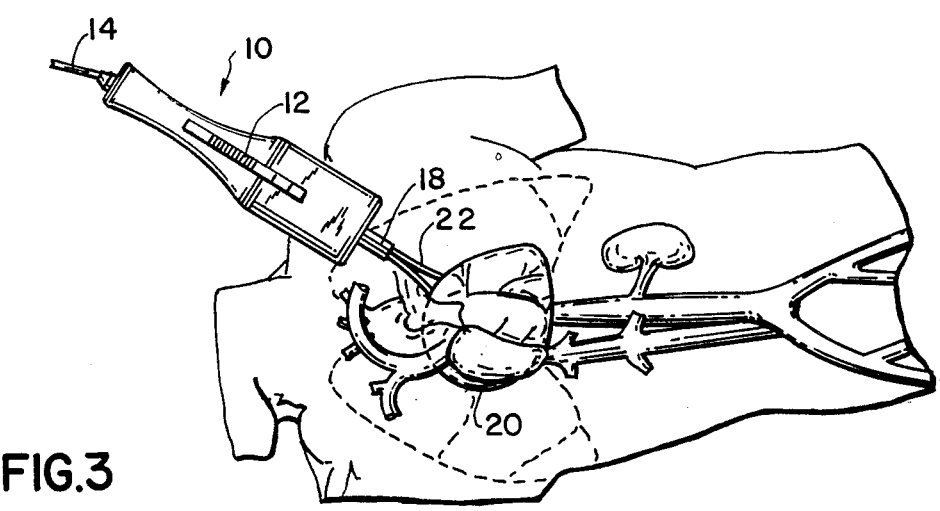
FIG. 3 is a vibratory device being utilized in open heart surgery.
Figure 6:
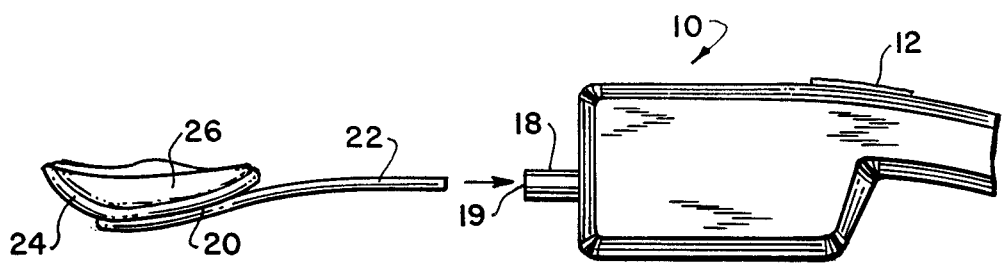

The heart cradle and support device, as shown in FIGS. 2 and 6, has a rigid plate 24 which is configured and so curved as to permit the heart to securely rest thereon through the intermediary of a soft and pliable contacting surface, such as a silicone bag 26. In this manner, the heart will be engaged on the underside thereof, as shown in FIG. 3 and supported on soft material backed by a heart conforming rigid backing member 24.

As is known from past experience, an ever present danger in open heart surgery is the possibility that air bubbles will remain in the papillary muscles of the heart after the patient is sutured following heart surgery. The previous method of patting and lightly agitating the heart in order to remove the trapped air bubbles therein did not ensure that all the air bubbles were removed. Consequently, the use of a vibrator that has a steady, and positive vibratory action, together with a specially adapted heart support for the vibrator arms, has greatly improved this technique.

Upon vibration by the present vibrator the surface tension of the air bubbles in the heart will be overcome and the bubbles will float to a common high point in the heart where they will be trapped in the papillary muscles. When this occurs, it is desirable for the surgeon to hand massage the heart in order to remove as much of the trapped air bubbles as possible. In the alternative, the surgeon may inject a hypodermic needle in the heart muscle. The hand massage procedure may be repeated if necessary, however, repetition will probably not be required if a hypodermic needle is used.

It should be observed from FIG. 6 that the heart engaging support 20 and the attached vibratory rods 22 can be removed from the vibrator instrument as a unit, and disposed of. Consequently, a plurality of heart cradling members may be employed by the surgeon who selectively chooses the heart cradling member which is more accurately sized for the specific heart patient. It should also be noted that it is possible to make the heart engaging surfaces of the heart cradling member to be stiff as well as soft, and to be permanent as well as disposable and replaceable.

It is also within the scope of the present invention to provide a secondary device such as a suction catheter or a needle attached to a syringe (not shown) for the suction of air from the heart, in conjunction with the use of the present vibrator device.

Referring to FIG. 2, it will be seen that the vibrator device is provided with the heart cradling attachment 20 which vibrates up and down as seen in both full lines and dashed lines. Consequently, when the heart, in open heart surgery, is placed in this device, the air bubbles entrapped in the papillae muscles will be released and will be taken away by suction catheters or other devices so that the serious or possibly fatal consequence of movement of air bubbles in the circulatory system will not be encountered.

Figure 4:
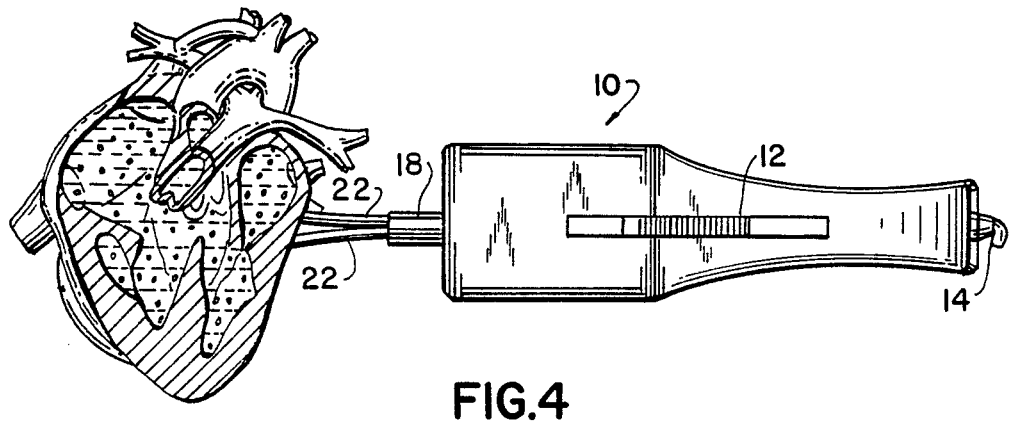
FIG. 4 is a vibratory device with the heart in place and illustrating the release of the air bubbles from the heart.
Figure 5:
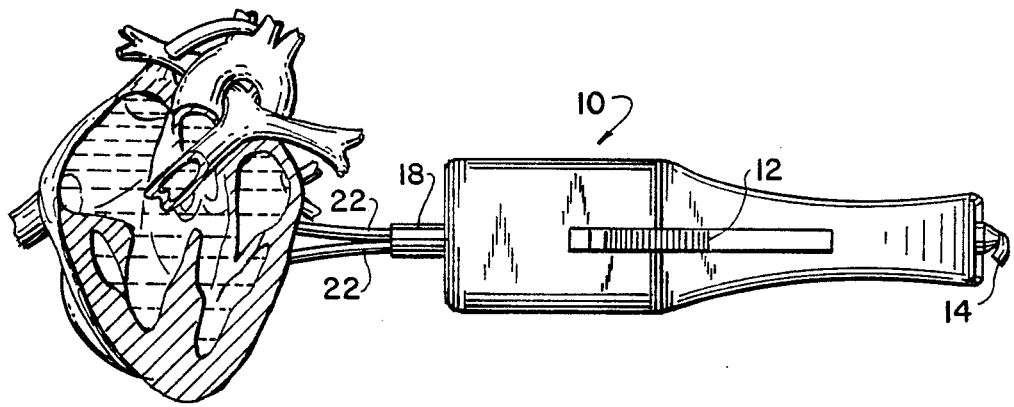
FIG. 5 is another elevational view showing the heart in place on the vibratory device and FIG. 6 shows the heart contacting or cradling member mounted on rods which are removable from the vibrator device.

The most desirable result of utilizing the present invention is that both the patient and the surgeon are assured that air bubbles present in the heart muscle will be expelled, and if there is a restriction in the operating room against the use of an alternating current source, a battery operated device may be employed, which will work effectively and achieve the required results. It should be observed that FIG. 4 shows the present device prior to use on the exposed heart in which air bubbles are present, while in FIG. 5, after the device is operative for a period of time, the air bubbles have been evacuated.

Figure 10:
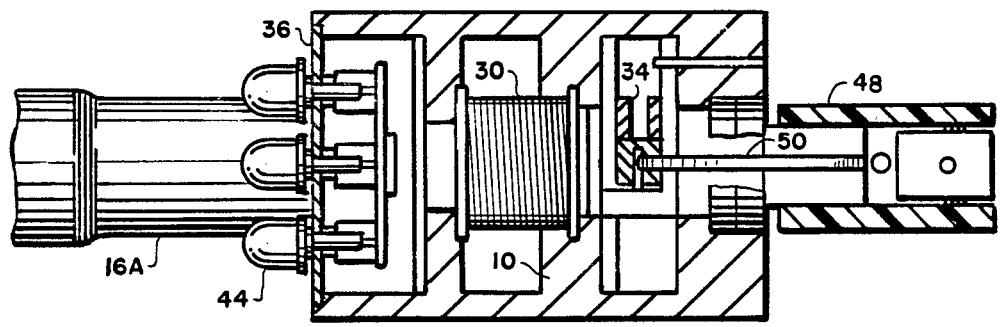
FIG. 10 is a partial sectional view of the vibratory device taken along the lines 10—10 of FIG. 7.
Figure 11:
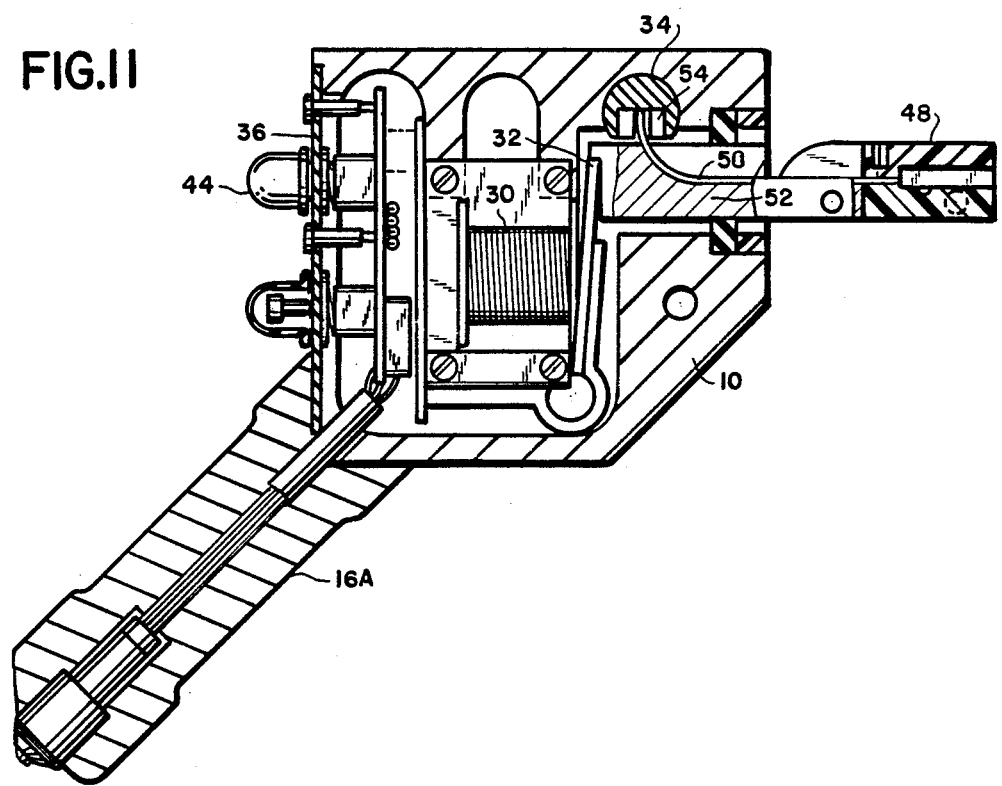
FIG. 11 is a partial side sectional view of the vibratory device shown in FIG. 10.

Referring now to FIG. 7-15 in which an alternate embodiment of the present invention is illustrated, the vibrator 10 is shown with a modified handle 16a in the form of a pistol grip having a line cord 14, and a strain relief 28. The operating mechanism of the vibrator 10 is more particularly shown in FIGS. 8 and 9, having a vibrator coil 30 and vibrator arm or spring 32. The vibrator 10 further incorporates a sensor 34, which may be of the photo-electric type, for a purpose hereinafter to be described. As seen in FIG. 10, as well as in FIGS. 10-12, a control panel 36 is shown whereby a master power switch 38 can be utilized for activating the power source different power levels may be selected to achieve different levels of vibration, such as switch 40 for low, and switch 42 for high levels. Various display light emitting diodes 44 indicate the active power level at any given time.

Referring to FIGS. 8 and 9, a cradle device 20, which is in a form of a elliptical, heart cradling spoon is provided with an elongated attachment arm 22a, having a dimple 46, located on the underside of the attachment arm 22a remote from the spoon 20. As can be seen from FIG. 7, 11 and 12, the attachment arm 22a can be removable inserted within a pivotable clamp 48 mounted on the exterior of the vibrator 10. As further seen in solid lines in FIG. 7, as well as in FIG. 14, when the clamp 48 is in its latched position, the dimple 46 is forced into recess 50 in the bottom portion 52 of the clamp 48. It should be apparent that when the cradle device arm 22 is removed from the clamp, said clamp functions as a destruct device so that the arm and spoon 20 can not be reused.

In order to make the cradle device or spoon 20 vibrate, it is necessary to operate a selected switch on the control panel 36 in order to apply AC power to the vibrator device. However, the vibrator coil or spring 32 will not vibrate until the arm 22a of the cradle device is inserted within the clamp 48 and an elongated wire 50, attached to the end of the arm 22 remote from the cradle device or spoon 20 is forced by the guide 52 in the space 54 to interrupt the beam of the sensor 34 and thus apply current to the vibrator coil 30.

It should be apparent that the present arrangement shown in FIGS. 7-15 is a convenient operating device for a physician engaged in heart massage. Moreover, the disposability of the heart engaging spoon device is of great benefit in utilizing a device of this type, as well as the option to select various power levels depending upon the type of heart messages required by the patient.

Figure 16:
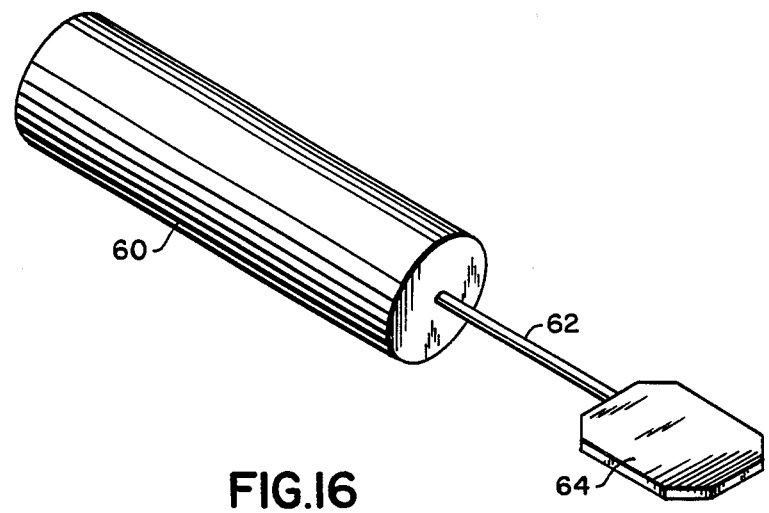
FIG. 16 is a top plan view of a further embodiment of the present invention.
Figure 17:
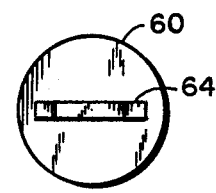
FIG. 17 is a front elevational view of the heart contacting vibrating member.

FIGS. 16 and 17 show an alternate embodiment of the present invention in which the vibratory device takes the form of a battery-operated oscillating unit 60 in which oscillations are transmitted through rod 62 to a relatively flat heart-contacting member 64. The member 64, because of its relatively small size and portability, permits the surgeon to place the instrument in tighter spaces within the body without having to lift the heart in order to place the same in a configured heart cradle. Thus, the heart may be contacted tangentially at selected locations by the contact member 64, which will still be effective to overcome the surface tension of air bubbles and the same will float to a common high point in the heart, as described herebefore in connection with the embodiment of the invention shown in FIGS. 1-3. In addition, the device of FIGS. 16 and 17 is more compact and lighter in weight than the previous described alternate constructions of the present invention.

While the invention has been disclosed and described herein with reference to a particular embodiment of the invention, it is apparent that variations and modifications may be made which will fall within the true spirit and scope of the invention as defined in the following claims:

We claim:

1. A vibratory device for releasing air bubbles trapped in the heart muscle during open heart surgery comprising: an electrically operated oscillating unit, at least one arm connected to said oscillating unit and provided with a heart engaging support member having a soft and pliable surface and a rigid backing member and conforms to the contiguration of at least part of the heart, and a power source for supplying vibrations to said heart engaging support member to thereby cause said arm and support member to vibrate gently thereby freeing said air bubbles from said heart.

2. A vibratory device as claimed in claim 1 wherein said soft and pliable surface for said heart engaging support is a silicone bag upon which the underside of the heart rests.

3. A vibrating device for releasing air bubbles trapped in the heart muscle during open heart surgery comprising: an electrically operated oscillating unit, a pair of arms removably connected to said oscillating unit, a curved heart engaging support plate secured to said arms, said plate having a soft and pliable surface and a rigid backing member and conforms to the configuration of at least part of the heart, and an electrical power source for supplying current to said oscillating unit to thereby cause said arms and support plate to vibrate gently, thereby freeing said air bubbles from said heart.

4. An arrangement for releasing air bubbles trapped in the heart muscle during open heart surgery comprising: a vibratory device including an electrically operated oscillating unit having at least one arm connected thereto and provided with a heart engaging support member having a soft and pliable surface and conforms to the configuration of at least part of the heart, and an electric power source for supplying current to said oscillating unit to thereby vibrate gently said arm and said support member causing the surface tension of the air bubbles in the heart to be broken whereby the bubbles will float in the heart to a common high point.

5. A vibratory device as claimed in claim 3 further comprising a pair of spaced bores in said vibrating device for receiving said removable arms provided with said support plate.

6. A vibratory device for releasing air bubbles trapped in the heart during open heart surgery comprising: an electrically operated oscillating unit provided with a clamp, a curved heart engaging support plate having a soft and pliable surface and a rigid backing member and conforms to the configuration of at least part of the heart and having an elongated arm with a projection at the end remote from said support plate, said arm being received in said clamp said clamp having a recess for receiving said projection, said clamp including means for rendering said arm and spoon unless responsive to removal of said arm from said clamp, and an electric power source for supplying current to said oscillating unit to cause said elongated arm and support plate to vibrate thereby freeing said air bubbles from the heart.

7. A vibratory device as claimed in claim 6 further comprising a sensor mounted in said oscillating unit which when activated causes current to flow to said oscillating unit, and means on the end of said elongated arm remote from said support plate for activating said sensor when said arm is inserted in said clamp and said projection is in said recess.

8. A vibratory device as claimed in claim 6 wherein said clamp is pivotally mounted on said oscillating unit from an open to a closed position and vice versa.

9. A vibratory device as claimed in claim 6 further comprising a control for said device having a plurality of selectable power levels for said oscillating unit.

* * * * *